(12) United States Patent
Raab

(10) Patent No.: US 11,458,033 B2
(45) Date of Patent: Oct. 4, 2022

(54) EXTENSION ASSIST DEVICE FOR AN ANATOMIC JOINT BRACE

(71) Applicant: Brian Raab, St. Gregor (SK)

(72) Inventor: Brian Raab, St. Gregor (SK)

( * ) Notice: Subject to any disclaimer, the term of this patent is extended or adjusted under 35 U.S.C. 154(b) by 733 days.

(21) Appl. No.: 15/067,706

(22) Filed: Mar. 11, 2016

(65) Prior Publication Data

US 2017/0112652 A1 Apr. 27, 2017

Related U.S. Application Data

(60) Provisional application No. 62/244,483, filed on Oct. 21, 2015.

(51) Int. Cl.
*A61F 5/01* (2006.01)

(52) U.S. Cl.
CPC .... *A61F 5/0125* (2013.01); *A61F 2005/0165* (2013.01); *A61F 2005/0179* (2013.01)

(58) Field of Classification Search
CPC ............ A61F 5/0125; A61F 2005/0167; A61F 2005/0179; A61F 5/0123; A61F 2005/0158; A61F 5/01; A61F 5/0102; A61F 5/0106; A61F 5/0118; A61F 5/013; A61F 5/0585; A61F 5/05858; A61F 5/373; A61F 2005/0132; A61H 1/0237; A61H 1/024; A61H 1/0274; A61H 1/0277
USPC .......... 602/16, 26, 5, 20, 21, 23, 27; 601/33, 601/34; 623/46; 403/120; 128/877, 878, 128/881, 882

See application file for complete search history.

(56) References Cited

U.S. PATENT DOCUMENTS

| 3,471,664 A | 10/1969 | Hansen | |
|---|---|---|---|
| 5,472,410 A | * 12/1995 | Hamersly | ............. A61F 5/0125 601/33 |
| 5,575,764 A | * 11/1996 | Van Dyne | ............. A61F 5/0125 482/124 |

FOREIGN PATENT DOCUMENTS

| CA | 2216198 | 5/1999 |
|---|---|---|
| EP | 0039578 | 11/1981 |
| GB | 2344769 | 6/2000 |

* cited by examiner

*Primary Examiner* — Caitlin A Carreiro
(74) *Attorney, Agent, or Firm* — Ryan W. Dupuis; Kyle R. Satterthwaite; Ade & Company Inc.

(57) ABSTRACT

An orthotic brace for an anatomic joint includes an upper brace portion for securement about an upper limb portion of the joint and a lower brace portion pivotally coupled to the upper brace portion for securement about a lower limb portion of the joint. A cable guide is pivotal relative to the lower brace portion and is operative between a working condition fixed for rotation with the upper brace portion relative to the lower brace portion and a released condition in which the upper brace portion pivots independently. A spring is coupled between the lower brace portion and a cable about the cable guide to bias towards an extended position in the working condition of the cable guide. Stops on the guide prescribe the range of biased motion in the working condition and independent stops on the brace portions prescribe the range of unbiased motion in the released condition.

16 Claims, 7 Drawing Sheets

EXTENSION ASSIST DEVICE FOR AN ANATOMIC JOINT BRACE

FIELD OF THE INVENTION

The present invention relates to orthotic braces to support anatomic joints, and more particularly the present invention relates to the field of mechanical orthotic braces that resist flexion of the joint, thereby biasing the joint towards an extended position.

BACKGROUND

Orthotic braces are traditionally used to support and/or limit the range of motion of an anatomic joint, such as a knee joint or elbow. A knee brace is frequently used to pivotally connect portions of the orthotic brace that are secured to the body above and below the knee joint. Such a knee brace permits relative movement of the upper and lower portions of the brace, while permitting flexion and extension of the leg to which the knee brace is attached.

The normal range of motion for a knee joint is considered to be 0° of extension and 135° of flexion, though in some people this may range from about −10° of extension to about 150° of flexion. Most functional activities require 0° to 117° of motion, while walking requires complete knee extension at heel strike and up to 60° degrees of flexion at the initiation of swing phase.

Individuals with an injury, such as an ACL tear, patellar dislocation, or quadriceps injury; or a medical condition, such as osteoarthritis, may experience difficulty with their knee buckling at a time of weight bearing. Knee buckling leads to a sudden loss of postural support that commonly results in a fall, which may lead to additional injuries such as fractures. For individuals with weak or ineffective quadriceps muscles, weight loading on a flexed knee can lead to knee buckling.

Various knee braces with extension assist have been described in the art, for example as taught in CA2216198 to Cruz, EP0039578 to Davis, GB2344769 to Hart, and U.S. Pat. No. 3,471,664 to Campbell et al. Each of these knee braces uses biasing means, typically one or more springs, to bias the knee joint towards an extended position.

However, there remains a desire for an anatomic joint brace with extension assist that allows the range of flexion to be readily adjusted to meet the needs of the user, for example based upon their size and/or anatomic joint strength; that can be preset to provide a set amount of resistance when the anatomic joint is in the full extension position; and that allows the user to readily release the resistance as needed to allow uninhibited flexion of the joint.

SUMMARY OF THE INVENTION

According to one aspect of the invention there is provided an orthotic brace for an anatomic joint having an upper limb portion and a lower limb portion which flex relative to one another about a joint axis, the orthotic brace comprising:
an upper brace portion for securement relative to the upper limb portion of the joint;
a lower brace portion for securement relative to the lower limb portion of the joint;
a pivotal coupling assembly connecting the upper brace portion to the lower brace portion for pivotal movement about a pivot axis for alignment with the joint axis between an extended position corresponding to an extended condition of the joint and a flexed position corresponding to a flexed condition of the joint; and
a biasing assembly for biasing the pivotal coupling assembly towards the extended position, the biasing assembly comprising:
a cable guide adapted to be fixed to a first one of the brace portions in a working condition of the cable guide;
a spring member having a first portion anchored relative to a second one of the brace portions;
a cable coupled at a first portion of the cable to a second portion of the spring member and supported at a second portion of the cable along a guide surface of the cable guide such that pivotal movement of the cable guide with the first one of the brace portions relative to the second one of the brace portions from the extended position towards the flexed position causes the cable to be flexed about the guide surface of the cable guide so as to resiliently deform the spring member and bias the brace portions to return to the extended position.

By providing a cable guide which pivots with one of the brace portions about which the cable is flexed as the brace portions are flexed relative to one another, an even and consistent biasing force is applied to the flexing of the joint of the user throughout the range of motion. By further arranging the cable guide to be releasable for unbiased pivotal coupling of the brace portions relative to one another, a set of stop portions between the cable guide and the second brace portion act to limit the range of biased motion, while an independent set of limit portions on the two brace portions can be provided for limiting the range of unbiased motion. Release of the coupling of the cable guide to the first brace portion thus accomplishes both i) release of the biasing and ii) release of the restricted range of biased motion by the corresponding stop portions, using a single actuation.

Preferably the spring member is linearly extended as the brace portions are displaced from the extended position to the flexed position.

Preferably the cable guide is fixed to the upper brace portion in the working condition, and the first portion of the spring member is anchored relative to the lower brace portion.

Preferably the cable guide is selectively operable between the working condition in which the cable guide is fixed relative to said first one of the brace portions, and a released condition in which said first one of the brace portions is movable relative to said second one of the brace portions independently of the cable guide such that the upper brace portion is pivotal about the pivot axis relative to the lower brace portion without biasing.

Preferably the cable guide is pivotal relative to said first one of the brace portions about the pivot axis in the released condition.

Preferably the guide surface of the cable guide comprises an arcuate guide surface having a center of curvature at the pivot axis.

An idler pulley wheel may be pivotally supported at a fixed location on said second one of the brace portions supporting a portion of the cable between the spring member and the cable guide to extend circumferentially about a portion of a periphery of the idler pulley wheel.

There may further be provided a screw member in threaded connection to said second one of the brace portions having a longitudinal axis oriented generally radially relative to the pivot axis, wherein the first portion of the spring member is anchored to the screw member such that adjustment of the screw member relative to said second one of the brace portions adjusts the tension of the spring member.

The spring member may comprise two helical springs mounted in parallel to one another between the cable and said second one of the brace portions.

To limit biased ranged of motion there may be provided a first stop portion on the cable guide and a second stop portion supported on said second one of the brace portions such that the stop portions are arranged to engage one another and limit relative pivotal movement between the brace portions within a prescribed biased range of motion in the working condition of the cable guide.

There further be provided an auxiliary guide which differs from the cable guide only by a configuration of the first stop portion thereof so as to correspond to a different prescribed biased range of motion, in which the auxiliary guide and the cable guide being readily interchangeable with one another.

Preferably the first stop portion comprises an arcuate slot having a centre of curvature at the pivot axis and the second stop portion comprises a pin which is slidably displaced between opposing ends of the arcuate slot as the brace portions are pivoted between the extended position and the flexed position.

The prescribed biased range of motion is preferably between 10° and 60°. For example, the overall range of motion under spring biased may be 10°, 20°, 30°, 40°, 50°, or 60°, although other ranges of motion may be desirable.

When the cable guide is readily configurable in a released condition in which the spring member is operatively disconnected from said first one of the brace portions for unbiased relative pivotal movement between the brace portions, the brace may further comprise a first limit portion on said first one of the brace portions independent of the first stop portion and a second limit portion on said second one of the brace portions independent of the second stop portion such that the limit portions are arranged to engage one another and limit relative pivotal movement between the brace portions within a prescribed unbiased range of motion in the released condition of the cable guide.

According to a second aspect of the present invention there is provided an orthotic brace for an anatomic joint having an upper limb portion and a lower limb portion which flex relative to one another about a joint axis, the orthotic brace comprising:

an upper brace portion for securement relative to the upper limb portion of the joint;

a lower brace portion for securement relative to the lower limb portion of the joint;

a pivotal coupling assembly connecting the upper brace portion to the lower brace portion for pivotal movement about a pivot axis for alignment with the joint axis between an extended position corresponding to an extended condition of the joint and a flexed position corresponding to a flexed condition of the joint; and a biasing assembly comprising:
a pivotal body which is selectively operable between a working condition in which the pivotal body is fixed relative to a first one of the brace portions and a released condition in which the pivotal body is pivotal relative to the first one of the brace portions about the pivot axis;
a biasing member operatively connected between the pivotal body and a second one of the brace portions whereby the biasing member biases the brace portions towards the extended position only in the working condition of the pivotal body;

a first stop portion supported on the pivotal body of the biasing assembly; and
a second stop portion supported on said second one of the brace portions so as to be arranged to engage one another and limit relative pivotal movement between the brace portions within a prescribed biased range of motion only in the working condition of the pivotal body.

There may also be provided an auxiliary body which differs from the pivotal body only by a configuration of the first stop portion thereof so as to correspond to a different prescribed biased range of motion, in which the auxiliary body and the pivotal body are readily interchangeable with one another.

The first stop portion may comprise an arcuate slot having a centre of curvature at the pivot axis and the second stop portion may comprise a pin which is slidably displaced between opposing ends of the arcuate slot as the brace portions are pivoted between the extended position and the flexed position.

In addition, there may be provided a first limit portion on said first one of the brace portions independent of the first stop portion and a second limit portion on said second one of the brace portions independent of the second stop portion such that the limit portions are arranged to engage one another and limit relative pivotal movement between the brace portions within a prescribed unbiased range of motion in the released condition of the cable guide.

The prescribed unbiased range of motion is preferably between 90° and 115°. For example, the overall range of unbiased motion may be 90°, 100°, 110°, or 115°.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
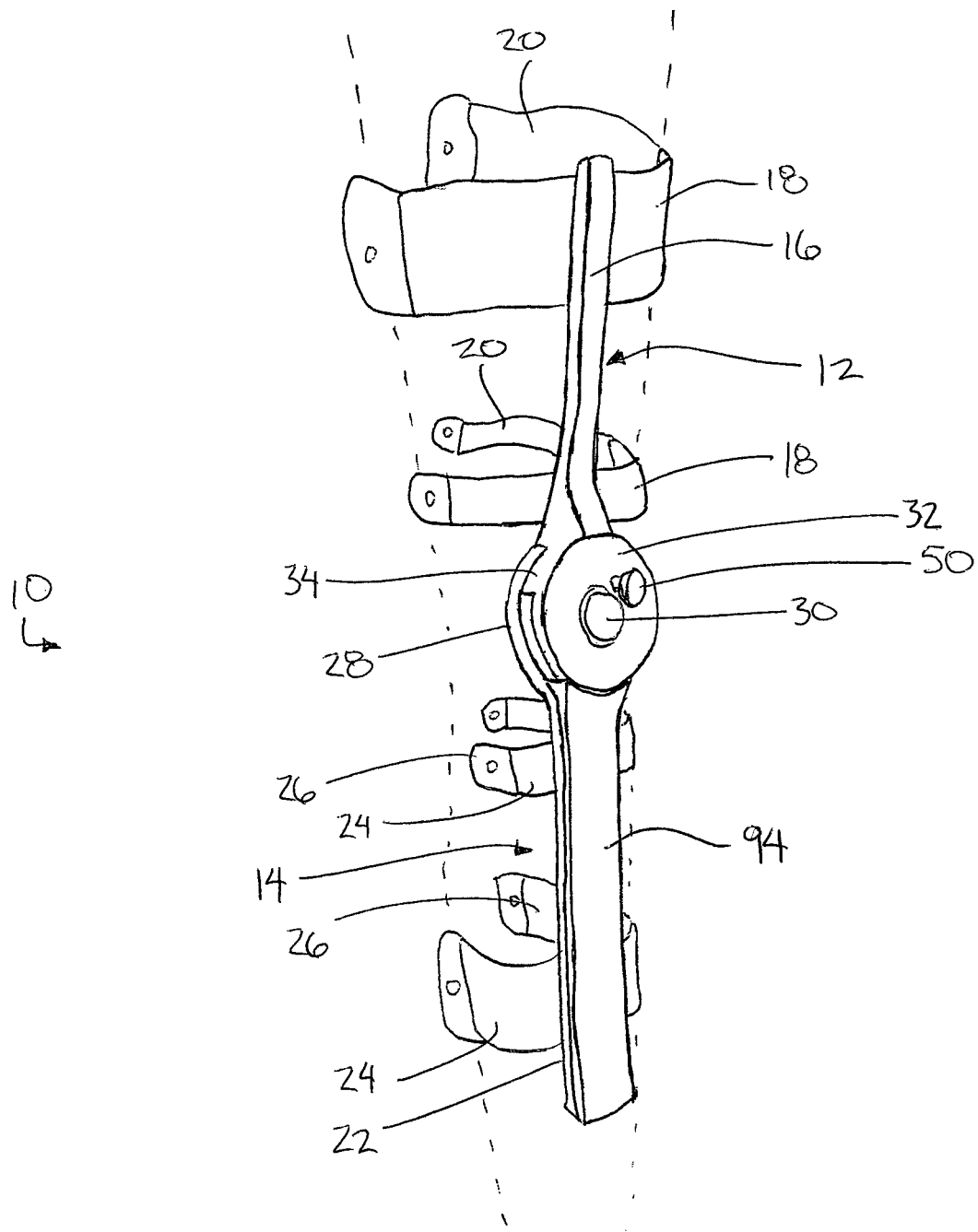
FIG. 1 is a perspective view of the brace.
Figure 2:
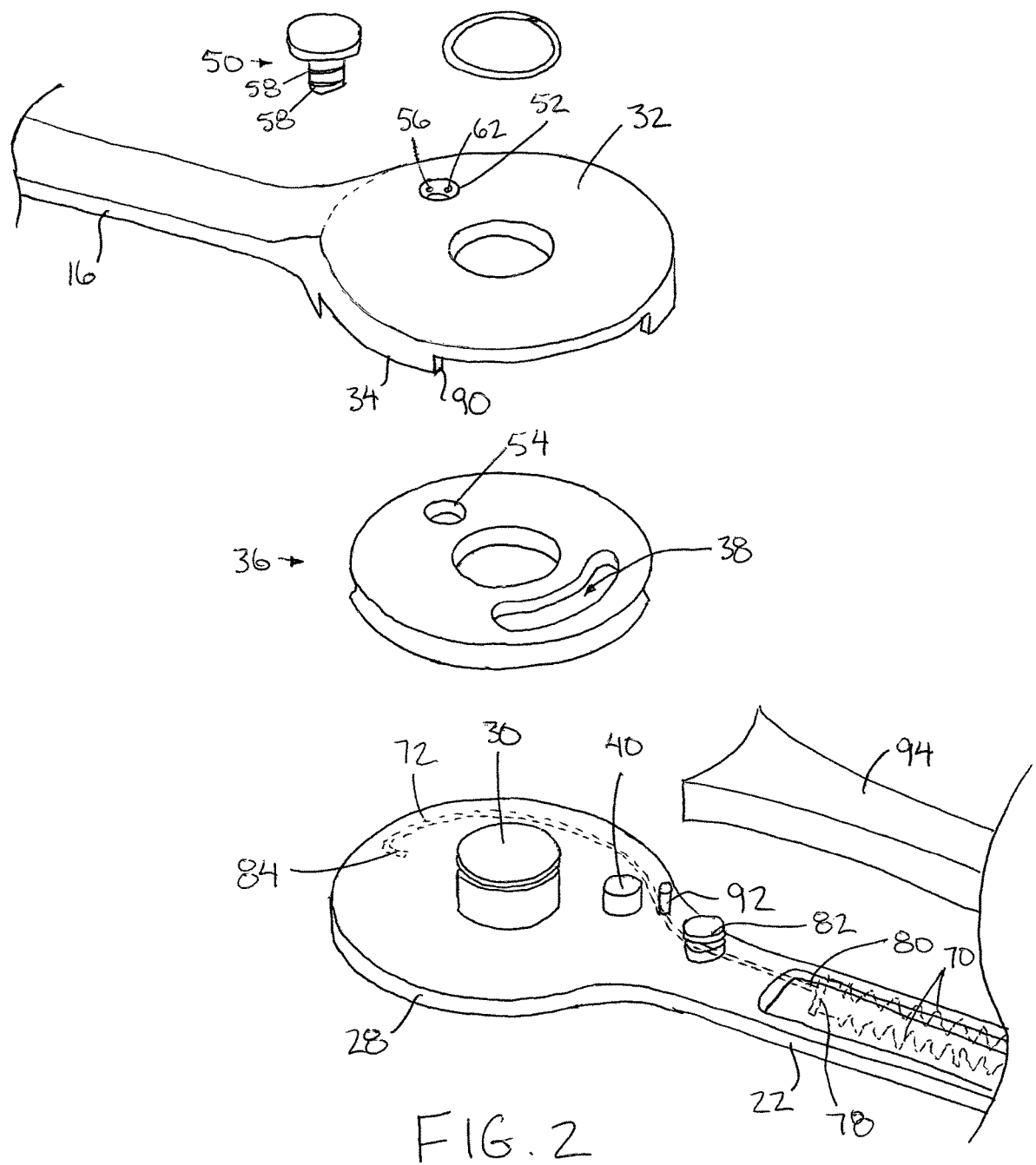
FIG. 2 is an exploded perspective view of the pivotal coupling between the upper and lower brace portions of the brace.
Figure 3:
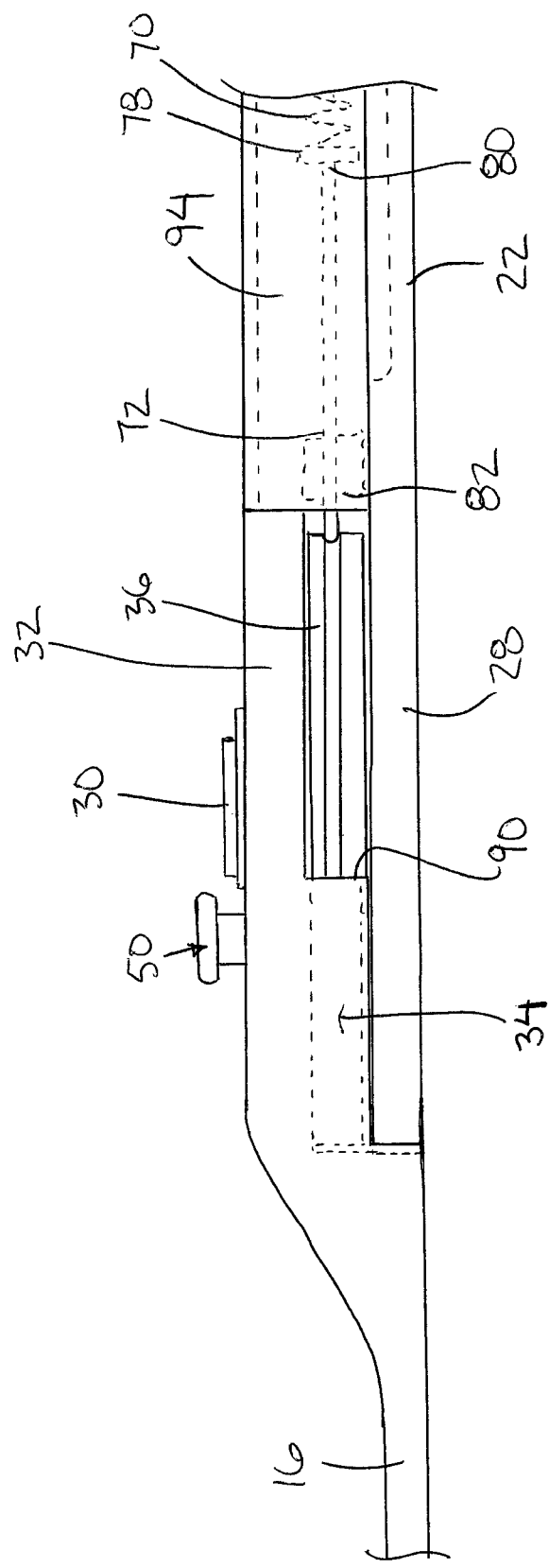
FIG. 3 is a side elevational view of the pivotal coupling of the brace in an extended position.
Figure 4:
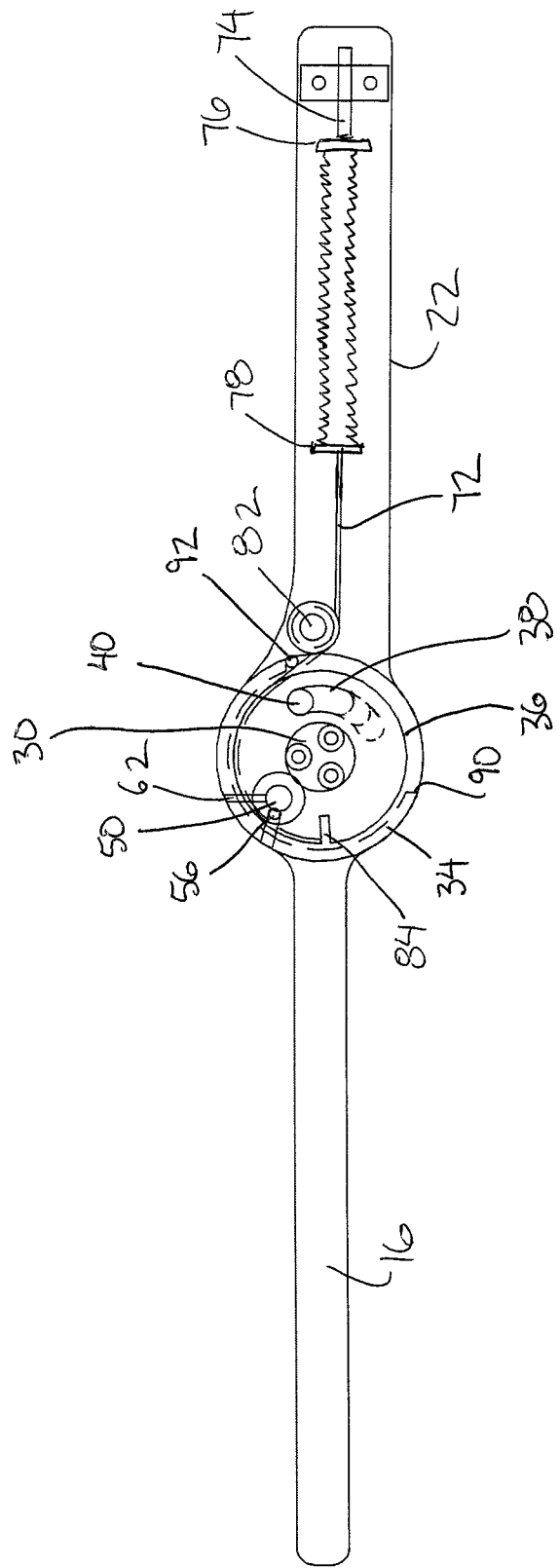
FIG. 4 is a schematic plan view of the brace in the extended position.
Figure 5:
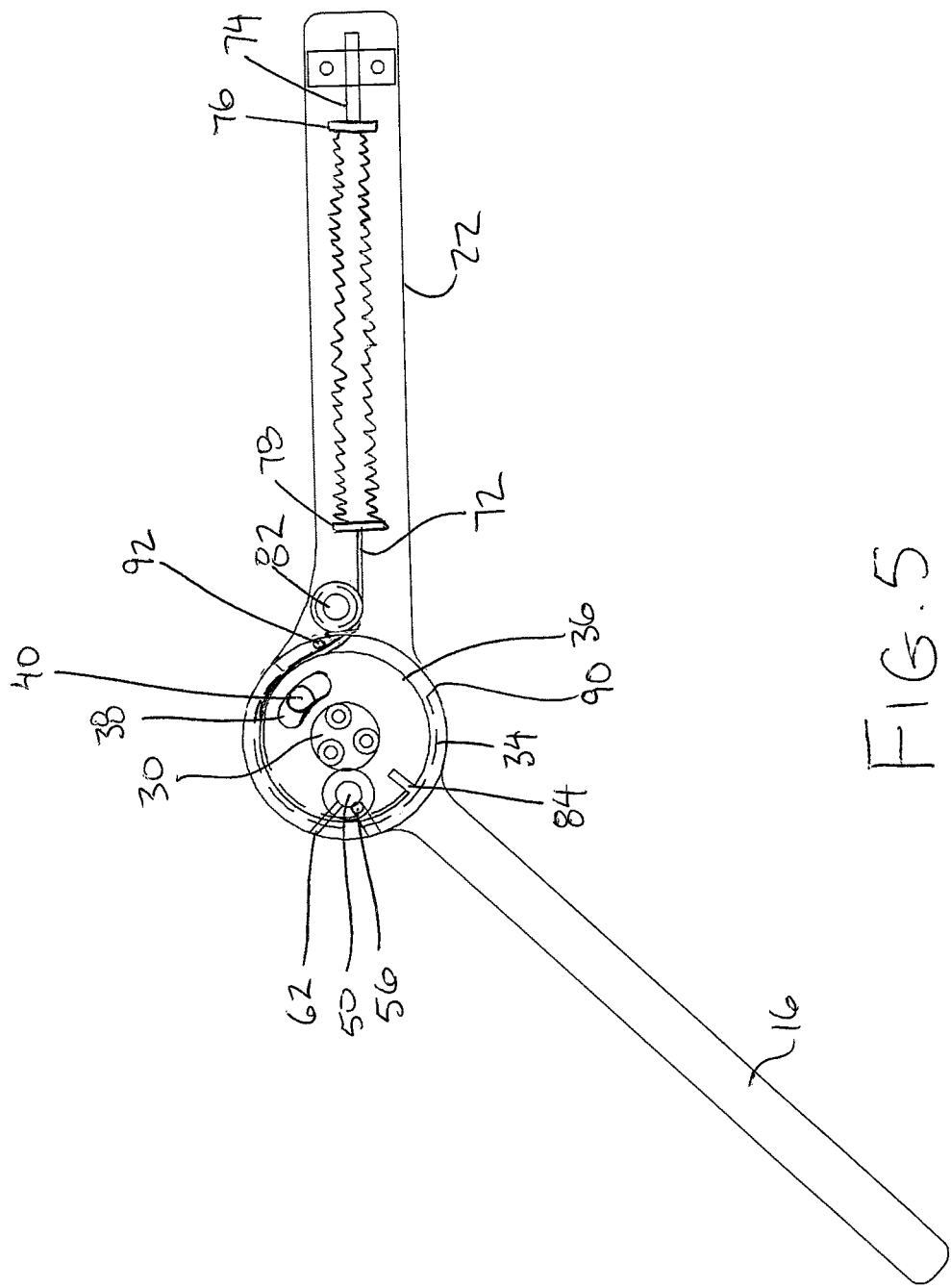
FIG. 5 is a schematic plan view of the brace in an intermediate position between the extended position and a flexed position.
Figure 6:
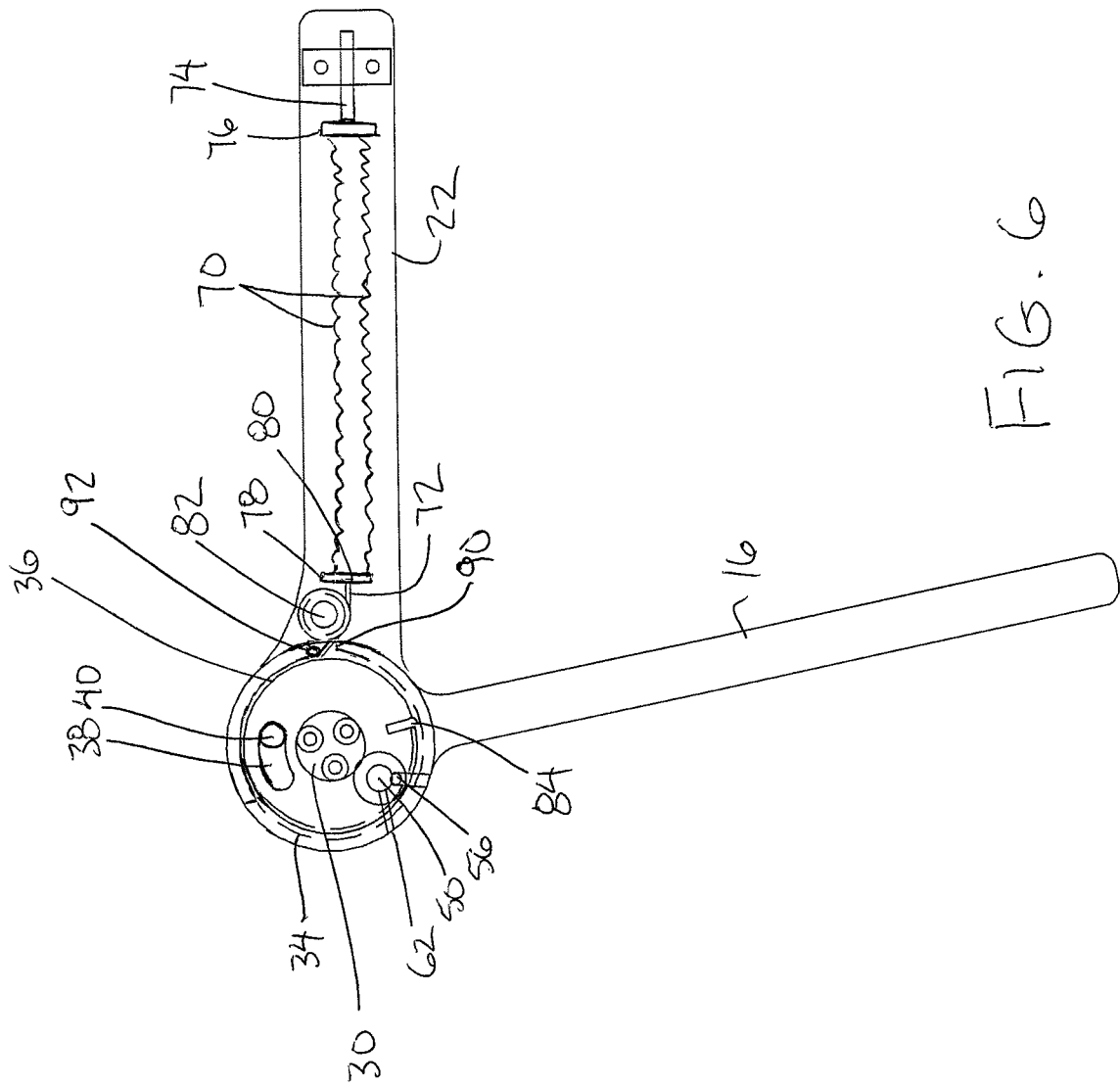
FIG. 6 is a schematic plan view of the brace in the flexed position.
Figure 7:
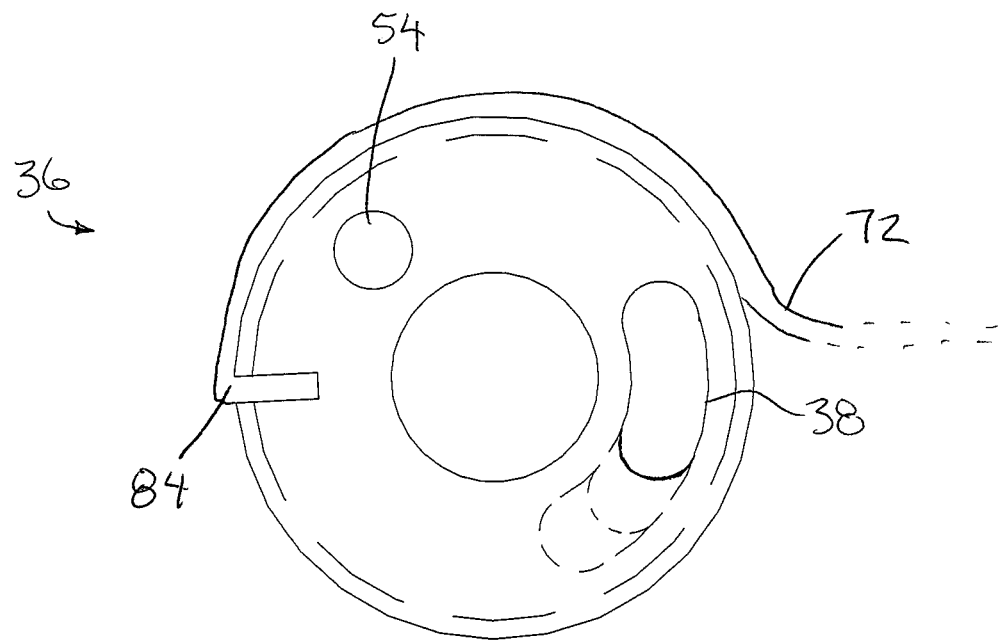
FIG. 7 is a plan view of the cable guide member.
Figure 8:
FIG. 8 is a side elevational view of the cable guide member.
Figure 9:
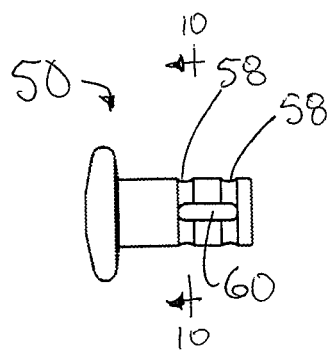
FIG. 9 is a side view of the coupling pin.
Figure 10:
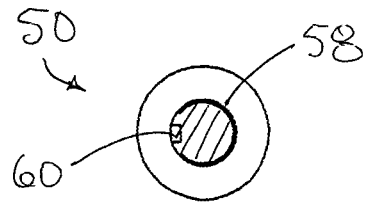
FIG. 10 is a section view along the line 10-10 of FIG. 9.

Referring to the accompanying figures, there is illustrated an extension assisting orthotic brace generally indicated by reference numeral 10. The brace 10 is particularly suited for use with an anatomical joint, for example a knee or an elbow, having an upper limb portion and a lower limb portion, for providing a biasing force to assist in extending the joint from a flexed condition to an extended condition of the joint.

The brace 10 generally includes i) an upper brace portion 12 for securement relative to the upper limb portion of the joint, ii) a lower brace portion 14 for securement relative to the lower limb portion of the joint, iii) a pivotal coupling between the upper and lower brace portions such that the upper and lower brace portions are pivotal relative to one another about a pivot axis for alignment with the joint axis between an extended position corresponding to an extended condition of the joint and a flexed position corresponding to a flexed condition of the joint, and iv) a biasing assembly for biasing the brace portions towards the extended position of the brace.

The upper brace portion 12 includes an elongated rigid arm oriented to extend generally radially outward from the pivot axis along a full length of the upper brace portion. Two anchor members 18 are provided at longitudinally spaced positions along the rigid arm 16. Each of the anchor members comprises a semi-circular body adapted to extend partway about a circumference the respective limb portion of the user. The rigid arm 16 is mounted centrally at an apex at the convex outer side of each anchor member such that the two anchor members are effectively curved about a common longitudinal axis of the limb portion received therein. A strap member 20 is associated with each anchor member to extend between opposing ends of the anchor member such that the strap member and the anchor member collectively form and annulus for adjustable securement about the full circumference of the respective limb portion of the user.

The lower brace portion 14 similarly comprises an elongate rigid arm 22 which includes two anchor members 24 mounted thereon having respective strap members 26 associated therewith in a manner substantially identical to the anchor members and strap members of the upper brace portion, but sized differently for a corresponding lower limb portion of the user to be received therein. The rigid arm 22 of the lower brace portion and the rigid arm 16 of the upper brace portion extend away from the pivot axis at diametrically opposed locations in the extended position.

All of the anchor members may be lined with a suitable resilient material for comfort against the body of the user.

The inner end of the rigid arm 22 of the lower brace portion nearest to the pivot axis is provided with a circular plate portion 28 oriented perpendicularly to and concentric with the pivot axis of the pivot coupling. The plate portion 28 mounts a pivot shaft 30 thereon at the pivot axis such that the cylindrical shape of the pivot shaft defines the pivot axis. The pivot shaft 30 is fastened with threaded fasteners in fixed relation to an outer side of the plate portion 28 in which the outer side is defined as the surface of the plate portion facing away from the joint of the user.

The inner end of the rigid arm 16 of the upper brace portion nearest to the pivot axis is also provided with a circular plate portion 32 which locates an aperture centrally therein which is sized to receive the pivot shaft therein. In a mounted configuration, the plate portion of the upper brace portion and the plate portion of the lower brace portion are parallel and spaced apart from one another along the pivot axis so as to be co-axial with one another. The aperture in the upper plate portion 32 receives the pivot shaft therein with the inner diameter of the aperture being approximately equal or slightly greater than the outer diameter of the pivot shaft such that the upper brace portion is freely pivotal relative to the pivot shaft of the lower brace portion.

An inner surface of the plate portion 32 facing inwardly towards the joint of the user is also suitably oriented to face inwardly towards the outer side of the plate portion 28 of the lower brace portion. The upper plate portion 32 integrally supports a perimeter wall portion 34 about a portion of the perimeter of the upper plate portion which protrudes inwardly from the inner surface of the upper plate portion towards the outer side of the lower plate portion 28. The perimeter wall portion 34 is generally cylindrical in shape yet only extends partway about the circumference of the two plate portions so as to form only a portion of a surface of a cylinder. The height of the perimeter wall portion 34 in the axial direction defines an axial gap between the inner surface of the upper plate portion 32 and the outer surface of the lower plate portion 28 in the assembled configuration.

The gap between the upper plate portion 32 and the lower plate portion 28 in the axial direction of the pivot shaft is occupied by a pivotal cable guide body 36, also referred to as a pivotal body, in the form of a generally cylindrical pulley wheel having an aperture centrally therein which is sized to receive the pivot shaft therethrough for rotatably supporting the cable guide body on the pivot shaft. The cable guide body 36 has a thickness in the axial direction which spans between the inner surface of the upper plate portion and the outer surface of the lower plate portion.

Once the cable guide body 36 and the upper plate portion 32 of the upper brace portion are both mounted onto the pivot shaft 30 of the lower brace portion, a snap ring is received within a circumferential groove at the outer end of the pivot shaft to maintain the components couples relative to one another along the pivot shaft.

The biasing assembly is operatively connected between the lower brace portion and the cable guide body 36. The cable guide body 36 is in turn arranged for operative connection to the upper brace portion in a working condition in which the upper brace portion is biased relative to the lower brace portion towards the extended position. The cable guide body 36 however can be readily released from the upper brace portion in a released condition in which the upper brace portion pivots relative to the lower brace portion independent of the cable guide body for pivoting of the upper brace portion relative to the lower brace portion without biasing as described in further detail below.

A coupling pin 50, also referred to as a coupling member, is received within an axially oriented bore 52 in the upper plate portion 32 for axial sliding relative to a corresponding axially oriented bore 54 in the cable guide body. More particularly the coupling pin 50 is slidable in the axial direction of the pivot axis at a location spaced radially outward from the pivot axis between the released condition supported only in the bore 54 of the upper plate portion such that the upper brace portion is pivotal relative to the cable guide body, and the working condition in which the coupling pin spans from the upper plate portion into the bore 54 in the cable guide body for coupling the cable guide body to the upper brace portion for pivotal movement together relative to the lower brace portion about the pivot shaft 30. The cable guide body and the upper brace portion move together in the working condition because they are held fixed, stationary, rigid and immovable relative to one another by the coupling member 50.

A spherical retainer ball 56 may be mounted within a corresponding cavity in the upper plate portion 32 at the circumference of the bore 52 so as to be urged by a spring to protrude into the circumference of the bore. A pair of retainer grooves 58 are mounted at axially spaced positions along the coupling pin such that one of the grooves aligns with the retainer ball 56 in the working condition and another one of the grooves is aligned with the retainer ball 56 in the released condition. The retainer ball serves to retain the coupling pin in a selected condition, however the spring force can be readily overcome to allow axial displacement between the working condition and the released condition as desired.

To prevent release of the coupling pin from the upper plate portion entirely, an axially oriented slot 60 is provided along one side of the coupling pin which receives the end of a set screw 62 threaded into the body of the upper plate portion 32 such that the inner end of the set screw protrudes inwardly into the circumference of the bore 52 to be received within the slot 60. Axial movement of the coupling pin is thus limited to a range of movement between the working condition and the released condition corresponding to the inner end of the set screw abutting axially opposed ends of the slot 60.

When the cable guide body is in the working condition as determined by the coupling pin, the overall permitted range of pivotal movement of the cable guide body relative to the lower brace portion is determined by a first stop portion on the cable guide body and a second stop portion on the lower brace portion. The first stop portion comprises an arcuate slot 38 formed in the cable guide body having a curvature centred on the pivot axis. The slot 38 extends through the full thickness of the cable guide body in the axial direction. The second stop portion provided on the lower plate portion 28 is in the form of a stop pin 40 which protrudes from the outer surface of the plate portion parallel to the pivot shaft by a height corresponding to the axial thickness of the cable guide body for alignment with the arcuate slot 38 within which it is received in the assembled configuration.

The length of the arcuate slot in the circumferential direction thus determines the overall biased range of movement in the working condition of the cable guide body 36. Typical arcuate slots are arranged to have an arc length in the order of 10°, 20°, 30°, 40°, 50° or 60° for example. Typically a plurality of cable guide bodies are available which are identical to one another in configuration with the exception of the length of the arcuate slot. The brace is initially assembled by selecting a cable guide body having an arc length corresponding to the desired range of biased movement to be provided to the user. If a different range of biased movement is subsequently desired, the user can simply interchange the cable guide body 36 with a different cable guide body having an arcuate slot of different arc length therein. One end of the arcuate slot for all cable guide bodies remains in the same location corresponding to the end of the slot abutting the stop pin 40 therein in the extended position of the brace with the bores 52 and 54 aligned with one another to enable the coupling pin to be displaced between the working and released conditions respectively.

Biasing is provided by two helical springs 70 which are mounted in parallel with one another to collectively define a spring member having a first portion anchored relative to the lower brace portion and a second portion coupled to a cable 72 which is in turn anchored relative to the cable guide body 36 as described in the following.

A screw member 74 in the form of a threaded tension shaft is mounted on the outer end of the rigid arm 22 of the lower brace portion in threaded connection with a radially oriented threaded bore on the rigid arm. Rotation of the screw member thus causes the screw member to be longitudinally displaced relative to the rigid arm 22 in a radial direction relative to the pivot axis of the brace. A first bridge 76 is mounted to the inner end of the tension shaft for coupling outer ends of the two springs 70 at laterally spaced positions thereon. The two springs 70 each comprise a helical spring which is wound helically about a longitudinal axis oriented in a radial direction relative to the pivot axis of the brace such that the longitudinal axes of the two helical springs are parallel and spaced apart from one another. A second bridge 78 is coupled to the opposing ends of the springs and serves to mount the first end 80 of the cable 72 centrally thereon between the anchoring points of the two springs 70.

An idler pulley wheel 82 is mounted at the inner end of the rigid arm 22 of the lower brace portion in close proximity to the circular plate portion 28 thereof such that the idler pulley wheel is rotatable about an axis which is parallel to the pivot axis of the brace. The main portion of the cable extends from the coupling to the two springs at the second bridge 78 in a radial direction towards the pivot axis. The cable extends about a portion of the circumference of the idler pulley wheel 82 at an intermediate location thereon between the spring member and the cable guide body 36. The cable then passes between the idler pulley wheel and the cable guide body to subsequently engage the outer periphery of the cable guide body 36.

A second end portion 84 of the cable extends circumferentially about the peripheral guide surface of the cable guide body through an arc of near 180° to the terminal and of the cable 72 which is anchored in fixed relation to the perimeter of the cable guide body 36 at a location diametrically opposite from the rigid arm of the lower brace portion in the extended position. In the working condition when the cable guide body pivots with the upper brace portion relative to the lower brace portion, pivoting of the cable guide body is in a direction which acts to flex a greater length of the cable about the cable guide body as the brace approaches the flexed position which pulls the first end of the cable radially inward towards the pivot axis and thereby linearly extend the springs. The extension of the springs causes the biasing force which urges the brace back towards the extended position.

Even though the springs apply continued pressure on the cable guide body, the cable guide body is prevented from pivoting beyond the extended position relative to the lower brace portion even when the coupling pin is released due to the stop pin 40 abutting the corresponding and of the arcuate slot 38. When the coupling pin 50 is in the working condition, the cable guide body moves together with the upper brace portion such that the upper brace portion can only be pivoted relative to the lower brace portion through the range of motion dictated by the arc length of the arcuate slot 38.

To release the biasing, and permit flexing of the upper brace portion relative to the lower brace portion beyond the prescribed range of biased motion dictated by the arcuate slot 38, the user can position the brace in the extended position and displace the coupling pin to the released condition thereof. The upper brace portion is then freely pivotal about the pivot shaft independent of the cable guide body and the range of biased motion dictated by the arcuate slot.

The range of motion of the upper brace portion relative to the lower brace portion in this unbiased and released state is determined by a first limit portion 90 on the upper brace portion and a second limit portion 92 on the lower brace portion which are independent of the first and second stop portions 38 and 40. The first limit portion 90 corresponds to the terminal ends of the perimeter wall 34 of the upper brace portion. A typical desired range of overall movement in an unbiased state of the brace is 115°, however the limit portions may be configured to define an unbiased range of movement of 90°, 100°, or 110° for example while still being effective.

The second limit portion 92 comprises a stop pin which is fixed on the outer side of the lower plate portion 28 near the inner end of the rigid arm in alignment with the perimeter wall of the upper brace portion. The second limit portion 92 is aligned with the gap in the circumferential direction in the perimeter wall 34 so as to abut and engage one end of the perimeter wall in the extended position and substantially abut the other end of the perimeter wall 34 in the fully flexed position corresponding to the maximum permissible flexion of the upper brace portion relative to the lower brace portion in an unbiased mode of operation. In the instance of an overall unbiased range of movement of 115°, the perimeter wall 34 extends in the circumferential direction through an arc of approximately 245° such that the gap in the circumferential direction between opposing ends of the perimeter wall corresponds approximately to an arc length of 115° to receive the stop pin defining the second limit portion 92 throughout the unbiased range of motion.

The perimeter wall 34 also provides the function of containing the cable guide body 36 mostly enclosed between the upper plate portion and the lower plate portion such that access to the cable extending about the cable guide body is substantially restricted by the location of the perimeter wall.

Each of the idler pulley wheel and the cable guide body include peripheral surfaces having a circumferentially oriented groove about the full circumference thereof which receives the cable therein to retain the cable on the perimeter guide surfaces thereof.

A cover 94 is provided for mounting on the outer side of the rigid arm of the lower brace portion such that the components of the biasing assembly and the first end of the cable are enclosed between the rigid arm 22 and the cover.

When configuring the brace for a user, a guide body 36 is first selected having an arc length which corresponds to the desired range of bias assist to be provided to the user. The selected pulley is then mounted on the pulley shaft and the cable and spring arrangement are connected followed by mounting of the upper brace portion on the pivot shaft to be retained with the snap ring as described above. With the coupling pin in the released condition, the upper brace portion can be freely pivoted relative to the lower brace portion through a full range of motion, for example corresponding to approximately 115°, as determined by interaction between the first limit portion 90 and the second limit portion 92. The cable guide body remains in the extended position relative to the lower brace member as the upper brace portion pivots relative to the lower brace portion.

When biasing assistance is desired, the brace is positioned in the extended position to align the bores of the coupling pin so that the coupling pin can engage the cable guide body 36 into a working condition of the cable guide body. Once in the working condition, pivoting of the upper brace portion relative to the lower brace portion from the extended position causes the cable guide body 36 to pivot with the upper brace portion for winding a greater portion of the cable about the peripheral guide surface of the cable guide body to linearly extend the springs in the radial direction relative to the pivot axis. Threaded adjustment of the screw member to which the springs are secured enables the amount of spring tension to be adjusted which in turn adjusts the amount of biasing force used to assist the user in returning the joint to the extended position.

A user typically initially sets up the brace with a more limited range of biased motion, however as strength in the joint increases, the spring force can be relaxed and/or the cable guide body can be interchanged with differently configured cable guide bodies to gradually increase the permissible range of biased motion.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. An orthotic brace for an anatomic joint having an upper limb portion and a lower limb portion which flex relative to one another about a joint axis, the orthotic brace comprising:
    an upper brace portion for securement relative to the upper limb portion of the joint;
    a lower brace portion for securement relative to the lower limb portion of the joint;
    a pivotal coupling assembly connecting the upper brace portion to the lower brace portion for pivotal movement about a pivot axis for alignment with the joint axis between an extended position corresponding to an extended condition of the joint and a flexed position corresponding to a flexed condition of the joint; and
    a biasing assembly comprising:
        a pivotal body which is selectively operable between a working condition in which the pivotal body is fixed relative to a first one of the brace portions and a released condition in which the pivotal body is pivotal relative to the first one of the brace portions about the pivot axis;
        a biasing member operatively connected between the pivotal body and a second one of the brace portions whereby the biasing member biases the brace portions towards the extended position only in the working condition of the pivotal body;
        a first stop portion supported on the pivotal body of the biasing assembly;
        a second stop portion supported on said second one of the brace portions so as to be arranged to engage the first stop portion and limit relative pivotal movement between the brace portions within a prescribed biased range of motion in the working condition of the pivotal body;
        a coupling member supported on a supporting one of the pivotal body and the first one of the brace portions so as to be movable relative to said supporting one of the pivotal body and the first one of the brace portions between the working condition and the released condition;
        wherein in the working condition the coupling member is coupled between the pivotal body and the first one of the brace portions such that the pivotal body is held fixed, stationary, rigid and immovable relative to the first one of the brace portions by the coupling member;
        whereby pivotal movement of the first one of the brace portions relative to the second one of the brace portions in the working condition of the coupling member causes: (i) the pivotal body to be pivoted relative to the second one of the brace portions, and (ii) the biasing member to be resiliently deformed to bias the brace portions towards the extended position;
        wherein in the released condition the coupling member is supported only on the supporting one of the pivotal body and the first one of the brace portions and is disengaged from another one of the pivotal body and the first one of the brace portions such that the pivotal body is pivotal relative to the first one of the brace portions;

whereby the first one of the brace portions is pivotal relative to the second one of the brace portions in an unbiased manner in the released condition of the coupling member.

2. The brace according to claim 1 wherein the biasing assembly further comprises:

the pivotal body comprising a cable guide;

the biasing member having a first portion anchored relative to the second one of the brace portions and an opposing second portion;

a cable coupled at a first portion of the cable to the second portion of the biasing member and supported at a second portion of the cable along a guide surface of the cable guide such that pivotal movement of the cable guide with the first one of the brace portions relative to the second one of the brace portions from the extended position towards the flexed position causes the cable to be flexed circumferentially about the guide surface of the cable guide so as to resiliently deform the biasing member and bias the brace portions to return to the extended position in the working condition.

3. The brace according to claim 2 wherein the cable guide is pivotal relative to said first one of the brace portions about the pivot axis in the released condition.

4. The brace according to claim 3 wherein the guide surface of the cable guide comprises an arcuate guide surface having a center of curvature at the pivot axis.

5. The brace according to claim 2 further comprising an idler pulley wheel pivotally supported at a fixed location on said second one of the brace portions supporting a portion of the cable between the biasing member and the cable guide to extend circumferentially about a portion of a periphery of the idler pulley wheel.

6. The brace according to claim 2 further comprising a screw member in threaded connection to said second one of the brace portions having a longitudinal axis oriented generally radially relative to the pivot axis, the first portion of the biasing member being anchored to the screw member such that adjustment of the screw member relative to said second one of the brace portions adjusts the tension of the spring member.

7. The brace according to claim 1 further comprising a first limit portion on said first one of the brace portions independent of the first stop portion and a second limit portion on said second one of the brace portions independent of the second stop portion such that the limit portions are arranged to engage one another and limit relative pivotal movement between the brace portions within a prescribed unbiased range of motion in the released condition of the pivotal body.

8. The brace according to claim 7 wherein the prescribed unbiased range of motion is between 90° and 115°.

9. The brace according to claim 1 in combination with an auxiliary body which differs from the pivotal body only by a configuration of the first stop portion thereof so as to correspond to a different prescribed biased range of motion, the auxiliary body and the pivotal body being readily interchangeable with one another.

10. The brace according to claim 1 wherein the first stop portion comprises an arcuate slot having a centre of curvature at the pivot axis and the second stop portion comprises a pin which is slidably displaced between opposing ends of the arcuate slot as the brace portions are pivoted between the extended position and the flexed position.

11. The brace according to claim 1 wherein the prescribed biased range of motion is between 10° and 60°.

12. The brace according to claim 1 wherein the coupling member is linearly slidable relative to said supporting one of the pivotal body and the first one of the brace portions between the working condition and the released condition thereof.

13. The brace according to claim 1 wherein the coupling member is slidable along a respective axis oriented parallel to the joint axis.

14. The brace according to claim 1 further comprising a limiting member defining a limited range of movement of the coupling member relative to said supporting one of the pivotal body and the first one of the brace portions between the working condition and the released condition thereof.

15. The brace according to claim 1 wherein the coupling member is slidably supported on the first one of the brace portions for movement between the working condition and the released condition relative to the pivotal body.

16. The brace according to claim 1 further comprising:

the first stop portion on the pivotal body and the second stop portion supported on said second one of the brace portions only engage one another to limit relative pivotal movement between the brace portions in the working condition of the body;

whereby the first stop portion and the second stop portion define a prescribed biased range of motion only in the working condition of the coupling member;

a first limit portion on said first one of the brace portions independent of the first stop portion;

a second limit portion on said second one of the brace portions independent of the second stop portion on the pivotal body;

the first limit portion and the second limit portion being arranged to engage one another and limit relative pivotal movement between the brace portions within a prescribed unbiased range of motion in the released condition of the cable guide;

the prescribed biased range of motion defined by the first and second stop portions in the working condition of the coupling member being independent of the prescribed unbiased range of motion defined by the first limit portion and the second limit portion in the released condition of the coupling member.

* * * * *